US008320986B2

(12) United States Patent
Huang et al.

(10) Patent No.: US 8,320,986 B2
(45) Date of Patent: *Nov. 27, 2012

(54) METHOD FOR DETERMINING THE RESOLUTION OF BLOOD GLUCOSE (75) Inventors: Yin-Chun Huang, Hsin-Chu (TW); Kuo-Jeng Wang, Kaohsiung (TW)

(73) Assignee: Transpacific Systems, LLC, Wilmington, DE (US)

( * ) Notice: Subject to any disclaimer, the term of this patent is extended or adjusted under 35 U.S.C. 154(b) by 1815 days.

This patent is subject to a terminal disclaimer.

(21) Appl. No.: 11/501,479

(22) Filed: Aug. 8, 2006

(65) Prior Publication Data
US 2007/0083336 A1 Apr. 12, 2007

Related U.S. Application Data (63) Continuation of application No. 10/771,333, filed on Feb. 5, 2004, now Pat. No. 7,089,122.

(30) Foreign Application Priority Data

Apr. 4, 2003 (TW) .............................. 92107792 A (51) Int. Cl.
*A61B 5/05* (2006.01)
*A61B 5/00* (2006.01)
*G01N 33/50* (2006.01)

(52) U.S. Cl. ...................... 600/347; 600/365; 702/19
(58) Field of Classification Search .................. 600/309, 600/345–366, 316, 322; 204/403.01, 403.02; 702/23, 19; 514/12; 435/193, 14
See application file for complete search history.

(56) References Cited

U.S. PATENT DOCUMENTS

| | | | |
|---|---|---|---|
| 3,837,922 A | 9/1974 | Ng et al. | |
| 4,005,002 A | 1/1977 | Racine et al. | |
| 4,129,478 A | 12/1978 | Racine et al. | |
| 4,274,832 A | 6/1981 | Wu et al. | |
| 4,299,493 A | 11/1981 | Harrison | |
| 4,407,290 A | 10/1983 | Wilber | |
| 4,407,959 A | 10/1983 | Tsuji et al. | |
| 4,420,564 A | 12/1983 | Tsuji et al. | |
| 4,444,743 A | 4/1984 | Yokoyama et al. | |
| 4,689,309 A | 8/1987 | Jones | |
| 4,731,726 A | 3/1988 | Allen, III | |
| 4,772,561 A | 9/1988 | Genshaw | |

(Continued)

FOREIGN PATENT DOCUMENTS

DE 1422172 1/1972

(Continued)

OTHER PUBLICATIONS

Uhegbu et al. "Analytical chemistry" 1993, 65, 2443-2451.

(Continued)

*Primary Examiner* — Navin Natnithithadha
(74) *Attorney, Agent, or Firm* — Stolowitz Ford Cowger LLP (57) ABSTRACT

The present invention provides a method for calculating the resolution of blood glucose which corresponding with the peak value of the rising curve. The average peak value is obtained from calculating the plurality of peak value, which determined after the pre-setting sampling time. Then, the average peak value is calculated with the resistance of the measuring circuit, reference resistance, and reference voltage to obtain the resolution of the blood glucose. Furthermore, the mapping table can be fabricated by the different height of maximum peak value and outputted voltage in different pre-setting sampling time, such that the resolution of blood glucose can be obtained in different outputted voltage values.

31 Claims, 4 Drawing Sheets

U.S. PATENT DOCUMENTS

| | | | |
|---|---|---|---|
| 4,791,066 A | 12/1988 | Ishiguro | |
| 4,805,624 A | 2/1989 | Yao et al. | |
| 4,850,805 A | 7/1989 | Madsen et al. | |
| 4,861,771 A | 8/1989 | Gaitanopoulos et al. | |
| 4,875,486 A | 10/1989 | Rapoport et al. | |
| 4,891,104 A | 1/1990 | Liston et al. | |
| 5,002,893 A | 3/1991 | Rosenthal et al. | |
| 5,198,367 A | 3/1993 | Aizawa et al. | |
| 5,222,495 A | 6/1993 | Clarke et al. | |
| 5,222,496 A | 6/1993 | Clarke et al. | |
| 5,246,002 A | 9/1993 | Prosser | |
| 5,284,845 A | 2/1994 | Paulsen | |
| 5,332,803 A | 7/1994 | Miyazaki et al. | |
| 5,337,745 A | 8/1994 | Benaron | |
| 5,341,805 A | 8/1994 | Stavridi et al. | |
| 5,344,832 A | 9/1994 | Cincotta et al. | |
| 5,362,966 A | 11/1994 | Rosenthal et al. | |
| 5,365,066 A | 11/1994 | Krueger, Jr. et al. | |
| 5,370,114 A | 12/1994 | Wong | |
| 5,407,545 A | 4/1995 | Hirose | |
| 5,420,108 A | 5/1995 | Shohet | |
| 5,468,755 A | 11/1995 | Cincotta et al. | |
| 5,494,562 A | 2/1996 | Maley | |
| 5,496,803 A | 3/1996 | Meier et al. | |
| 5,500,374 A | 3/1996 | Wenzhi | |
| 5,532,602 A | 7/1996 | Wiget | |
| 5,554,623 A | 9/1996 | Cincotta et al. | |
| 5,585,347 A | 12/1996 | Meier et al. | |
| 5,592,086 A | 1/1997 | Weinstock | |
| 5,616,558 A | 4/1997 | Ohneda et al. | |
| 5,666,956 A | 9/1997 | Buchert | |
| 5,700,776 A | 12/1997 | Ohneda et al. | |
| 5,772,586 A | 6/1998 | Heinonen et al. | |
| 5,814,600 A | 9/1998 | Rink et al. | |
| 5,882,935 A | 3/1999 | Hirai et al. | |
| 5,899,855 A | 5/1999 | Brown | |
| 5,997,476 A | 12/1999 | Brown | |
| 6,011,984 A | 1/2000 | Van Antwerp et al. | |
| 6,024,488 A | 2/2000 | Wu | |
| 6,024,699 A | 2/2000 | Surwit et al. | |
| 6,091,976 A | 7/2000 | Pfeiffer et al. | |
| 6,246,992 B1 | 6/2001 | Brown | |
| 6,312,924 B1 | 11/2001 | Presnell et al. | |
| 6,317,700 B1 | 11/2001 | Bagne | |
| 6,350,431 B1 | 2/2002 | Snow et al. | |
| 6,355,788 B1 | 3/2002 | Conklin et al. | |
| 6,361,985 B1 | 3/2002 | Conklin et al. | |
| 6,379,301 B1 | 4/2002 | Worthington et al. | |
| 6,416,988 B1 | 7/2002 | Conklin et al. | |
| 6,428,704 B1 | 8/2002 | Setoguchi et al. | |
| 6,434,409 B1 | 8/2002 | Pfeiffer et al. | |
| 6,558,351 B1 | 5/2003 | Steil | |
| 6,560,471 B1 | 5/2003 | Heller | |
| 6,616,819 B1 * | 9/2003 | Liamos et al. | 204/403.02 |
| 6,641,533 B2 | 11/2003 | Causey, III et al. | |
| 6,749,740 B2 * | 6/2004 | Liamos et al. | 205/792 |
| 6,942,518 B2 * | 9/2005 | Liamos et al. | 439/495 |
| 7,089,122 B2 | 8/2006 | Huang et al. | |
| 7,347,925 B2 * | 3/2008 | Hsieh | 205/777.5 |
| 2002/0133064 A1 | 9/2002 | Ueno et al. | |
| 2003/0150724 A1 | 8/2003 | Kawanaka et al. | |
| 2004/0126832 A1 | 7/2004 | Wang | |
| 2004/0210401 A1 | 10/2004 | Huang | |
| 2005/0235345 A1 | 10/2005 | Mitchell | |

FOREIGN PATENT DOCUMENTS

| | | |
|---|---|---|
| JP | 61020680 | 1/1986 |
| JP | 2000060803 | 2/2000 |
| TW | 357517 | 5/1999 |
| TW | 091138108 | 12/2002 |
| WO | 0011205 | 3/2000 |

OTHER PUBLICATIONS

Stolowitz Ford Cowger LLP; Related Case Listing; Sep. 13, 2010; 1 Page.

Pilosof et al. "Analytical Chemistry", 1982, 54, 1698-1701.

Life Scan One Touch Blood Glucose Monitoring System, Owner's Manual, www.lifescan.com/company/about/lsbkgrndr, 79 pages, Oct. 12, 2005.

Boland, Elizabeth et al., Limitations of Conventional Methods of Self-Monitoring of Blood Glucose, Diabetes Care, vol. 24, No. 11, pp. 1858-1862, Nov. 2001.

Gowenlock, Alan et al., Varley's Practical Clinical Biochemistry, pp. 320-332, 1988.

File History of U.S. Appl. No. 10/771,333, filed Feb. 5, 2004.
File History of U.S. Appl. No. 10/316,049, filed Dec. 11, 2002.
File History of U.S. Appl. No. 11/468,968, filed Aug. 31, 2006.
File History of U.S. Appl. No. 11/469,402, filed Aug. 31, 2006.
File History of U.S. Appl. No. 10/410,292, filed May 10, 2003.
File History of U.S. Appl. No. 11/695,967, filed May 3, 2007.

* cited by examiner

METHOD FOR DETERMINING THE RESOLUTION OF BLOOD GLUCOSE

This application is a continuation of U.S. patent application Ser. No. 10/771,333, filed Feb. 5, 2004, now U.S. Pat. No. 7,089,122 and entitled METHOD FOR DETERMINING THE RESOLUTION OF BLOOD GLUCOSE.

BACKGROUND OF THE INVENTION

1. Field of the Invention

The present invention generally relates to a method for determining the concentration of blood glucose, and more particularly to a method for determining a peak value of a rising curve to determine the concentration of blood glucose.

2. Description of the Prior Art

In the past, many systems have been developed for monitoring blood characteristics. For example, devices have been developed which are capable of determining such blood characteristics as blood oxygenation, and blood glucose concentration. However, significant difficulties exist when attempting to specifically determine blood glucose concentration accurately using noninvasive blood monitoring systems such as by means of spectroscopic measurement.

The difficulty in determining blood glucose concentration accurately may be attributed to several causes. Firstly, within the bloodstream, the blood glucose is typically found in very low concentrations (e.g., on the order of 100 to 1000 times lower than hemoglobin) so that such low concentrations are difficult to detect noninvasively, and require a very high signal-to-noise ratio. Additionally, with spectroscopic methods, the optical characteristics of glucose are very similar to those of water that is found in a very high concentration within the blood. Thus, where optical monitoring systems are used, the optical characteristics of water tend to obscure the characteristics of optical signals due to glucose within the bloodstream.

Furthermore, dry phase reagent test strips incorporating enzyme-based compositions are used extensively in clinical laboratories, physicians' offices, hospitals, and homes to measure the concentration of the compositions in the biological fluids. These strips have, for example, measured glucose, cholesterol, proteins, ketones, phenylalanine, or enzymes in blood, urine, or saliva. Measuring glucose concentration in samples of whole blood is a particularly common use. In fact, test strips have become an everyday necessity for many of the nation's several million people with diabetes.

Some test strips contain a testing reagent that turns a different shade of color depending on the concentration of glucose in a blood sample that has been applied to the strips. The blood glucose concentration is measured by inserting a strip into a meter that is basically a reflectance photometer, which determines the concentration from the change in color caused by the reaction between the testing reagent and blood glucose. The testing reagent typically contains an enzyme, such as glucose oxidase, which is capable of oxidizing glucose to glucose acid lactone and hydrogen peroxide; an oxidizable dye; and a substance having peroxidative activity, which is capable of selectively catalyzing oxidation of the oxidizable dye in the presence of hydrogen peroxide.

SUMMARY OF THE INVENTION

An object of the present invention is to provide a method for calculating the concentration of blood glucose by the relationship between a rising curve and the blood glucose concentration. The concentration of the blood glucose could be obtained from calculating these known values which include the slope on the peak point, resistance, reference resistance, reference voltage, and the average peak value obtained from calculating the plurality of peak values after a pre-set sampling time.

It is another object of the present invention to obtain the maximum of the peak values by using the property of the first differential of the peak value being greater than zero.

Another object of the present invention is to obtain the different heights of the peak values after different pre-set sampling times and using them to make a mapping table.

It is a further object of the present invention to determine the blood glucose concentration according to the different voltages en in the mapping table.

According to the above-mentioned objects, the present invention provides a method of determining the concentration of the blood glucose corresponding with the peak value of the rising curve. The peak value of the rising curve is the basis for determining the blood glucose concentration in the present invention. The concentration of the blood glucose could be obtained from calculating the given values, which include the slope on the peak point, resistance of the determining circuit, reference resistance, reference voltage, and the average peak value obtained from calculating the plurality of peak values after the pre-set sampling time. Furthermore, the mapping table can be created by recording the variable peak values corresponding to the variable pre-set sampling times, and referencing the mapping table to obtain the different concentration of blood glucose for different output voltages.

BRIEF DESCRIPTION OF DRAWINGS

The foregoing aspects and many of the advantages of this invention will become more readily appreciated as the same becomes better understood by reference to the following detailed description, when taken in conjunction with the accompanying drawings.

DESCRIPTION OF THE INVENTION

An appropriate and preferred embodiment will now be described in this section. It should be noted, however, that this embodiment is merely an example and can be variously modified without departing from the scope of the present invention. The present invention provides a performance method described as follows:

First, the blood glucose solution is placed on the test strip with the test reagent or catalyst such as an enzyme, wherein the test reagent will react with the blood glucose solution to generate the oxidation reduction reaction to generate an analog source. Then, the analog source is input into a determining circuit of a determining meter that converts an analog signal from the analog source into a digital signal, and then outputs the digital signal to a display apparatus.

Figure 1:
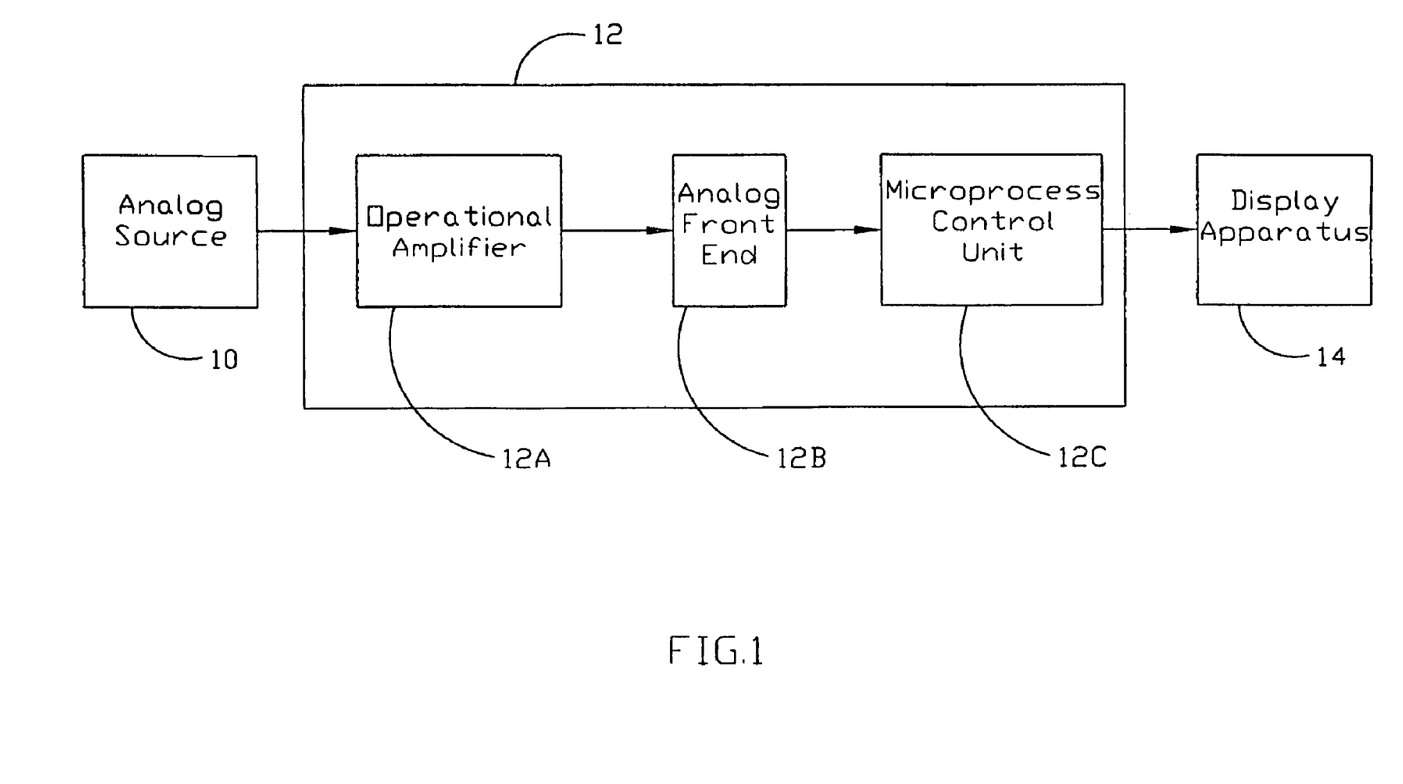
FIG. 1 is a schematic diagram showing how the peak value is used to determine the concentration of the blood glucose in accordance with a method disclosed herein.

Referring to FIG. 1, a schematic diagram shows the steps for determining the blood glucose concentration by utilizing the peak value. Reference number 10 denotes the analog source, which is generated from the chemical reaction between the blood glucose solution and the test reagent with the enzyme that acts as a catalyst. A treatment device 12 receives the analog signal from the analog source, converts the analog signal into a digital signal, and outputs the results from the digital signal into a display apparatus 14. The treatment device comprises an OA (Operational Amplifier) 12A with at least one resistor. When the blood glucose concentration increases, the OA resistance is also increases. The analog signal from the OA is converted by an AFE (Analog Front End) 12B into the digital signal. The AFE 12B can be an ADC (Analog to Digital Converter). Next, the digital signal from the AFE 12B is processed by a MCU (Microprocessor Control Unit) 12C. The processed digital signal is output from the MCU 12C to the display apparatus 14. The display apparatus 14 then displays is a curve diagram.

Figure 2:
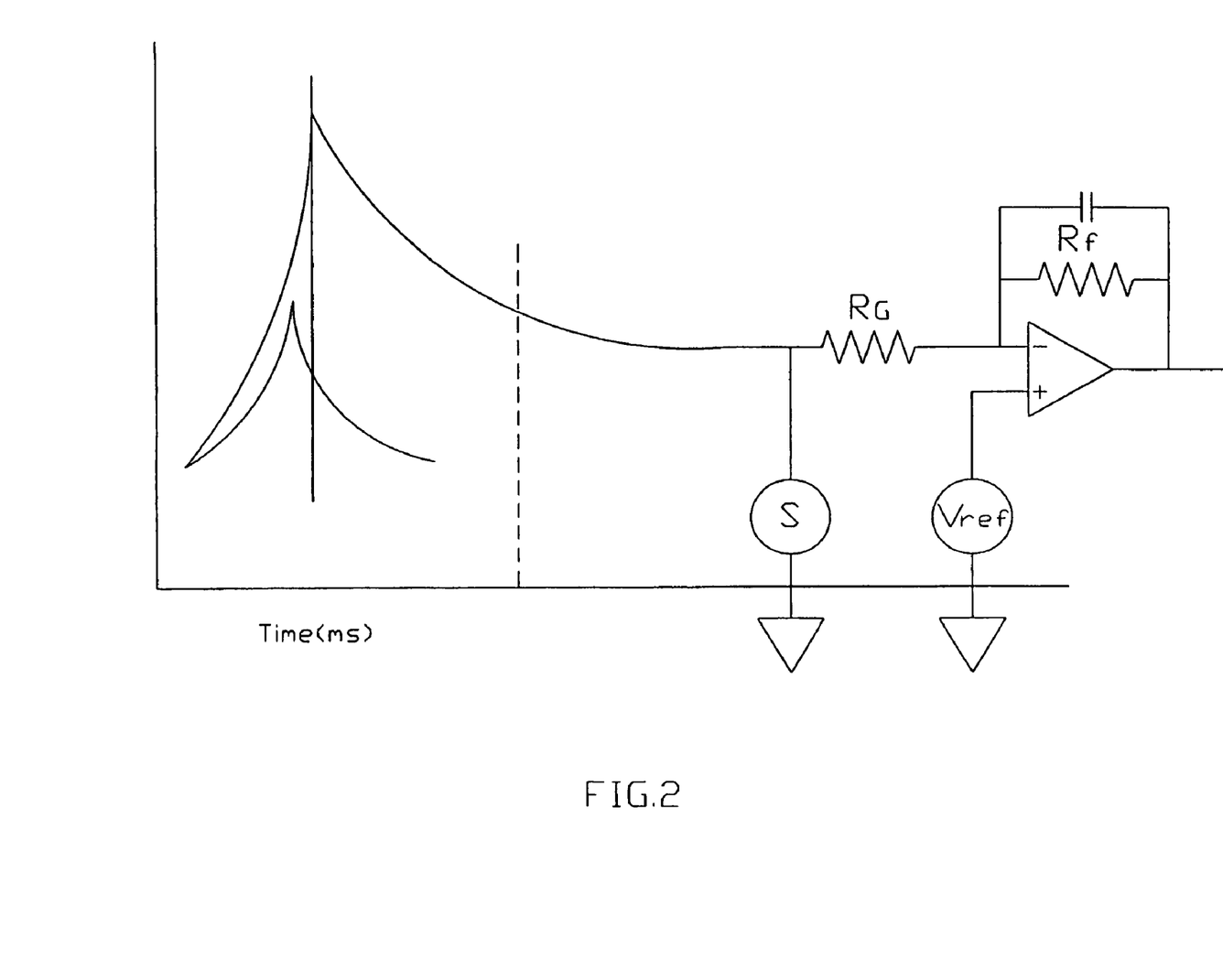
FIG. 2 is a schematic diagram showing the relationship between the rising curve and the operation amplifier in accordance with a method disclosed herein.

FIG. 2 is a schematic diagram illustrating the relationship between the rising curve of the blood glucose concentration and the operational amplifier. The blood glucose solution reacts with the test reagent to produce the analog signal. The height of the analog curve is determined by the blood glucose concentration and the resistance, the resistance increasing with the increase of the blood glucose concentration. After the analog signal is transferred into the operation amplifier, the analog signal will be transformed into the output voltage ($V_{out}$) according to known values: the slope on the peak point, the resistance ($R_G$) in the operational amplifier, the reference resistance ($R_f$), and the reference voltage ($V_{ref}$).

Figure 3:
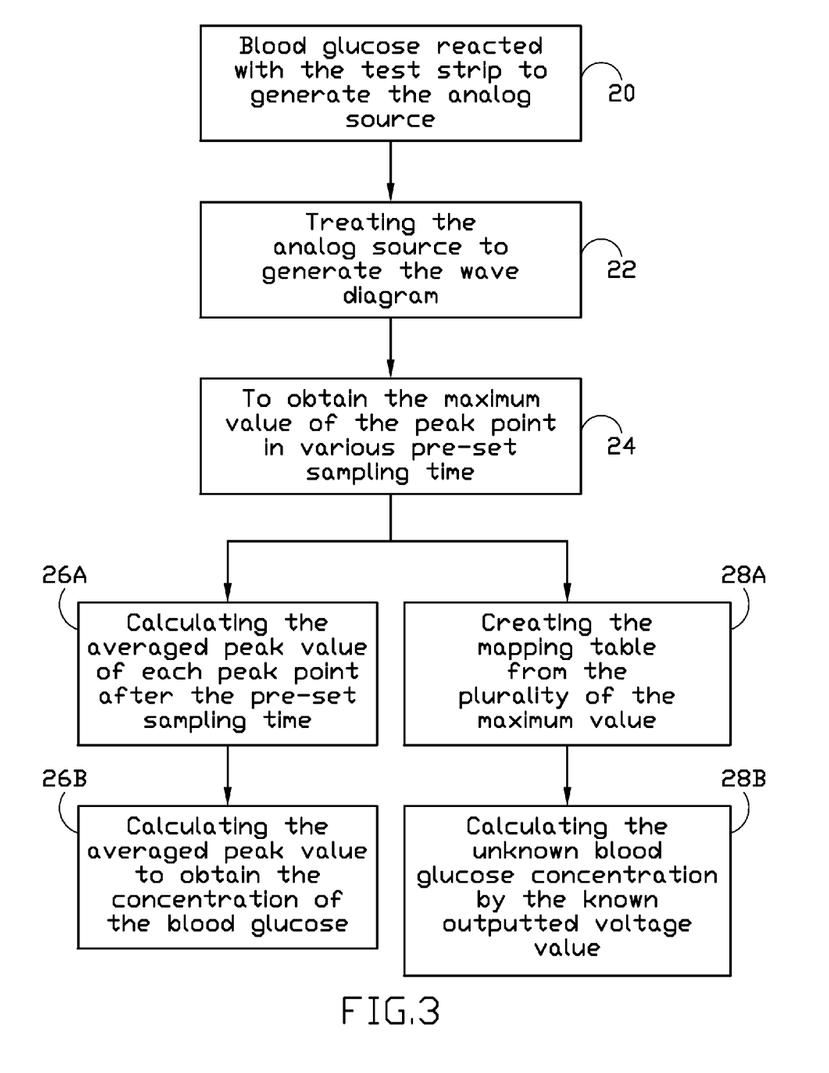
FIG. 3 is a flow chart showing the steps for determining the concentration of the blood glucose by using the peak value in accordance with a method disclosed herein.

FIG. 3 is a schematic diagram illustrating the flow steps for determining the blood glucose concentration from the peak value. In step 20 the blood glucose solution reacts with the catalyst to produce the analog signal. The chemical reaction may be an oxidation reduction reaction. Step 22 treats the analog signal source and produces a wave diagram. At step 24, the maximum value of the wave diagram is obtained after the pre-set sampling time. In the first preferred embodiment of the present invention, the average peak value could be calculated at step 26A from the plurality of peak values after the pre-set sampling time. At step 26B, the method determines the blood glucose concentration by calculating the average peak value. In the other preferred embodiment at step 28A, a mapping table is created from the plurality of peak values.

The mapping table shows the relationship between the blood glucose concentration and the output voltage. At step 28B, the blood glucose concentration is calculated by obtaining the output voltage value of an unknown blood glucose solution and comparing it with the mapping table.

Figure 4:
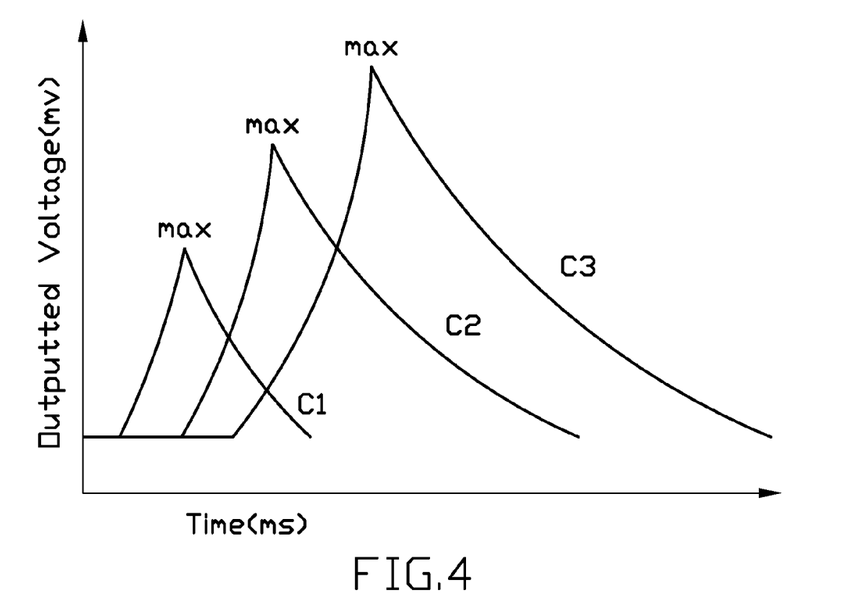
FIG. 4 is a schematic diagram showing the rising curve of the blood glucose concentration in accordance with a method disclosed herein.

FIG. 4 is a schematic diagram illustrating the rising curve of the blood glucose concentration. The peak value is obtained after the pre-set sampling time when the first differential is larger than zero, $y(t_1)-y(t_0)>0$, which is the difference between the first time ($t_1$) and the initial time ($t_0$) with a result that is larger than zero. In the first preferred embodiment of the present invention, the average peak value could be obtained by adding and averaging the plurality of peak values after the pre-set sampling time. After calculating the average peak value, the slope of the peak point, resistance, reference resistance, and reference voltage, are used for obtaining the blood glucose concentration.

Figure 5:
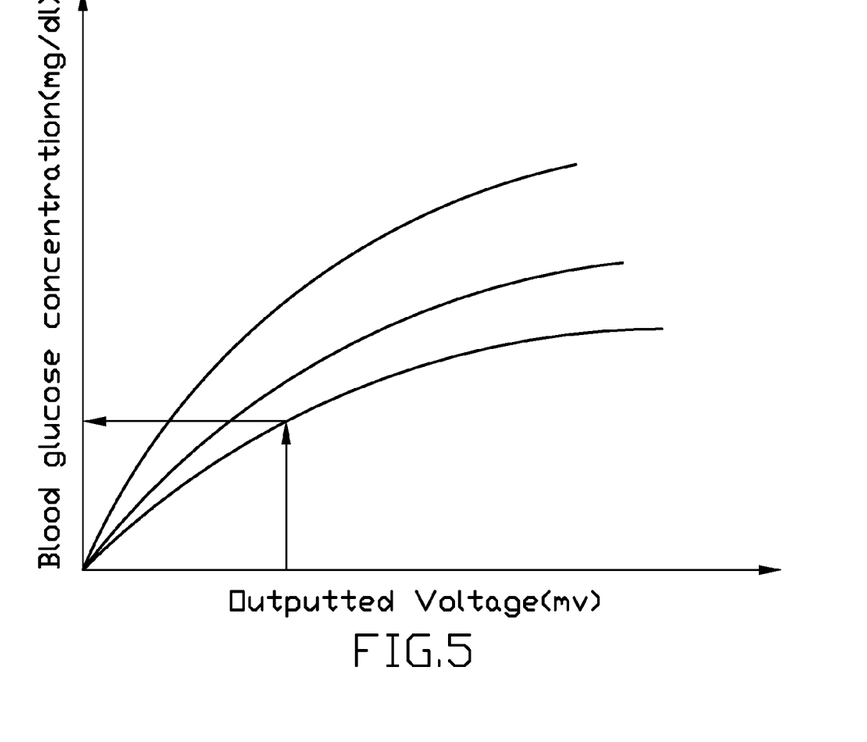
FIG. 5 is a schematic diagram showing the rising curves for the different blood glucose concentration solutions in accordance with a method disclosed herein.

FIG. 5 is a schematic diagram illustrating the rising curves of the different concentrations of the blood glucose solutions.

In FIG. 5, curves C1, C2 and C3 represent the different blood glucose concentrations. Likewise, if the first differential is larger than zero, the method of the present invention identifies the peak value of the curve and creates a mapping table of the output voltage and blood glucose concentration from the plurality of peak values. Therefore, the actual blood glucose concentration is obtained from the output voltage value of an unknown blood glucose solution by finding the corresponding value in the mapping table.

While this invention has been described with reference to illustrative embodiments, the description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method, comprising:
   obtaining an analog signal corresponding to a blood glucose solution;
   converting the analog signal into a digital signal;
   storing the digital signal into a memory device;
   calculating, using a processing device, an average peak value by averaging approximate local maximum values for a plurality of rising curves obtained from corresponding digital signal stored in the memory device during predetermined sampling times; and
   determining, using the processing device, a concentration of blood glucose in the blood glucose solution according to the average peak value.

2. The method of claim 1, wherein the analog signal is generated, at least in part, in response to application of the blood glucose solution on a test strip having a catalyst.

3. The method of claim 2, wherein the analog signal is further generated, at least in part, in response to an oxidation reduction reaction occurring on the test strip.

4. The method of claim 1, further comprising processing the analog signal with an AFE (Analog Front End).

5. The method of claim 1, wherein each approximate local maximum value comprises a difference between a first time ($t_1$) and an initial time ($t_0$) when the difference is larger than zero.

6. A method for determining a blood glucose concentration, comprising:
   receiving, at a processing device, at least one signal corresponding to a reaction from a blood glucose solution identifying at least one rising curve for the at least one signal;
   determining an approximate local maximum value of each of the at least one rising curve for the at least one signal during a sampling time; and
   comparing, using the processing device, the approximate local maximum value of the at least one rising curve with other rising curves stored in a mapping table on a memory device to identify the concentration of blood glucose associated with the blood glucose solution, wherein the other rising curves in the mapping table are associated with different known concentrations of blood glucose.

7. The method of claim 6,
   wherein the signal corresponds, at least in part, to an oxidation reduction reaction.

8. The method of claim 6, further comprising processing the signal with an AFE (Analog Front End).

9. The method of claim 8, further comprising increasing a resistance in the AFE as the concentration of blood glucose in the blood glucose solution increases.

10. The method of claim 8, further comprising using a reference resistance in the AFE.

11. The method of claim 8, further comprising using a reference voltage in the AFE.

12. The method of claim 6, wherein said determining the approximate local maximum value of the at least one signal comprises determining when a first differential of the at least one rising curve is larger than zero.

13. An apparatus, comprising:
an amplifier circuit configured to receive at least one analog signal corresponding to a blood glucose reaction;
a transforming circuit configured to transform the at least one analog signal into at least one digital signal; and
a control unit configured to determine a blood glucose concentration according to an average peak value by averaging an approximate maximum value of each of a plurality of rising curves measured during a sampling time, wherein the plurality of rising curves corresponds to each of the at least one digital signal.

14. The apparatus of claim 13, wherein the at least one analog signal corresponds to a chemical reaction created by placing a blood glucose solution on a test strip, wherein the test strip includes a catalyst.

15. The apparatus of claim 14, wherein the chemical reaction comprises an oxidation reduction reaction.

16. The apparatus of claim 13, wherein the transforming circuit comprises an analog front end (AFE).

17. The apparatus of claim 13, wherein the approximate maximum value comprises a difference between a first time and an initial time, and wherein the difference comprises a value larger than zero.

18. The apparatus of claim 13, wherein the control unit is further configured to use a mapping table that associates a voltage corresponding to the approximate maximum values from each of the plurality of rising curves.

19. A system, comprising:
means for receiving a signal corresponding to a blood glucose reaction;
means for converting the signal into data identifying an average peak value, wherein the average peak value comprises an average of approximate maximum values for a plurality of rising curves obtained during a sampling time; and
means for determining a concentration of blood glucose according to the identified average peak value of the rising curve.

20. The system of claim 19, wherein the signal is generated by a chemical reaction in response to placing a blood glucose solution on a test strip, wherein the test strip comprises a catalyst.

21. The system of claim 20, wherein the chemical reaction comprises an oxidation reduction reaction.

22. The system of claim 19, wherein the means for converting comprises an AFE (Analog Front End).

23. The system of claim 19, wherein the approximate maximum value comprises a difference between a first time and an initial time, and wherein the difference comprises a value larger than zero.

24. The system of claim 19,
wherein the means for determining is further configured to use a mapping table to determine the concentration of blood glucose; and
wherein the mapping table maps different known concentrations of blood glucose with corresponding approximate maximum values.

25. An apparatus, comprising:
a measuring circuit configured to measure a signal generated in response to a reaction with a blood glucose solution; and
a control unit configured to calculate an average peak value by averaging approximate local maximum values for a plurality of rising curves associated with the signal after a pre-set sampling time and calculate a blood glucose concentration of the blood glucose solution according to the average peak value.

26. The apparatus of claim 25, further comprising a test strip configured to produce the signal.

27. The apparatus of claim 25, wherein the test strip includes a catalyst configured to create an oxidation reduction reaction.

28. The apparatus of claim 25, wherein the measuring circuit comprises a resistor, a reference resistor, and a reference voltage.

29. The apparatus of claim 25, further comprising a transforming circuit configured to convert the signal from analog to digital.

30. The apparatus of claim 25, wherein the approximate local maximum value comprises a difference between the signal at a first time and at an initial time, and wherein the difference comprises a value larger than zero.

31. The apparatus of claim 25, wherein the control unit is further configured to determine the concentration of blood glucose based, at least in part, on how fast the signal reaches the corresponding approximate local maximum value.

\* \* \* \* \*

UNITED STATES PATENT AND TRADEMARK OFFICE
CERTIFICATE OF CORRECTION

PATENT NO. : 8,320,986 B2
APPLICATION NO. : 11/501479
DATED : November 27, 2012
INVENTOR(S) : Huang et al.

It is certified that error appears in the above-identified patent and that said Letters Patent is hereby corrected as shown below:

On the Title Page, Item (54), and in the Specification, Column 1, Line 2, Title, delete "RESOLUTION" and insert -- CONCENTRATION --, therefor.

On the Title Page, Item (56), under "OTHER PUBLICATIONS", in Column 2, Line 1, delete "et al." and insert -- et al., --, therefor.

On the Title Page, Item (57), under "ABSTRACT", in Column 2, Line 2, delete "resolution" and insert -- concentration --, therefor.

On the Title Page, Item (57), under "ABSTRACT", in Column 2, Line 11, delete "resolution" and insert -- concentration --, therefor.

On Title Page 2, Item (56), under "OTHER PUBLICATIONS", in Column 2, Lines 1-2, delete "Stolowitz Ford Cowger LLP; Related Case Listing; Sep. 13, 2010; 1 Page." and insert -- Stolowitz Ford Cowger LLP, Related Case Listing, Sep. 13, 2010, 1 Page. --, therefor.

On Title Page 2, Item (56), under "OTHER PUBLICATIONS", in Column 2, Line 3, delete "Pilosof et al." and insert -- Pilosof et al., --, therefor.

On Title Page 2, Item (56), under "OTHER PUBLICATIONS", in Column 2, Line 10, delete "Varley's Practical Clinical Biochemestry," and insert -- "Varley's Practical Clinical Biochemistry," --, therefor.

In the Specification

In Column 2, Line 14, delete "voltages en" and insert -- voltages --, therefor.

In Column 2, Line 54, delete "DESCRIPTION" and insert -- DETAILED DESCRIPTION --, therefor.

Signed and Sealed this
Eighteenth Day of June, 2013

Teresa Stanek Rea
*Acting Director of the United States Patent and Trademark Office*

CERTIFICATE OF CORRECTION (continued)
U.S. Pat. No. 8,320,986 B2

In the Claims

In Column 4, Line 25, in Claim 1, delete "into" and insert -- in --, therefor.

In Column 5, Line 38, in Claim 18, delete "values" and insert -- value --, therefor.